United States Patent [19]

Arkles

[11] Patent Number: 4,918,200
[45] Date of Patent: Apr. 17, 1990

[54] CHROMOGENIC AND FLUOROGENIC SILANES AND USING THE SAME

[75] Inventor: Barry C. Arkles, Ambler, Pa.

[73] Assignee: Huls America Inc., Piscataway, N.J.

[21] Appl. No.: 4,713

[22] Filed: Jan. 20, 1987

Related U.S. Application Data

[63] Continuation-in-part of Ser. No. 631,036, Jul. 16, 1984, abandoned.

[51] Int. Cl.$^4$ ............................................. C07D 311/04
[52] U.S. Cl. .................................... 549/214; 549/283; 549/285; 549/288; 549/289
[58] Field of Search ............... 549/214, 283, 285, 288, 549/289; 436/500, 546, 800

[56] References Cited

U.S. PATENT DOCUMENTS

| | | | |
|---|---|---|---|
| 4,182,856 | 1/1980 | Buckler | 436/545 |
| 4,279,992 | 7/1981 | Boguslaski et al. | 435/810 |
| 4,463,099 | 7/1984 | Baroncelli et al. | 436/546 |
| 4,659,657 | 4/1987 | Harnisch et al. | 549/285 |

OTHER PUBLICATIONS

Hengge et al., Monatshefte fur Chemie 104, 1071–76 (1973) by Springer-Verlag.

Ghose, "Carbonfunctional Organosilicon, etc.", Z. Naturforsch. 34B, 1140–1144 (1979).

Eaborn et al., "The Preparation of Some 4-Organosilicon, etc.", J. Organomet. Chem. 65 (1974) 169–179.

Buckler et al, I, "Optical Indicator, etc.", CA 102: 20796s (1984).

Kamat et al., "A Versatile Total Synthesis, etc.", CA 97: 109769m (1982).

Primary Examiner—Richard L. Raymond
Assistant Examiner—Patricia L. Morris
Attorney, Agent, or Firm—Davis Hoxie Faithfull & Hapgood

[57] ABSTRACT

Chromogenic or fluorogenic silanes are formed in which a reactive organosilane is coupled to a chromogenic or fluorogenic nucleus of the coumarin class of compounds, by an ether, urethane or urea linkage. The preferred compounds have the general formula.

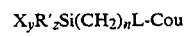

$$X_y R'_z Si(CH_2)_n L\text{-Cou}$$

wherein X is a displaceable or hydrolyzable group which allows the silanes to derivatize protic materials; R' is an aliphatic or aromatic hydrocarbon group; L is an ether (O), urethene (NCO) or urea (NCN) linkage; Cou is a coumarin derivative; n=1 to 8; y=1 to 3 and Z=0 to 2, such that y plus z equal 3. The ether linked silanes may be formed by hydrosilylation of an alkenyl ether of the coumarin compound, while the urethane or urea linked silanes may be formed by the direct reaction of a reactive silylisocyanate with a hydroxyl- or amine-substituted coumarin compound. The silanes are useful in derivatizing protic materials to provide the protic materials with chromogenic or fluorogenic properties.

7 Claims, No Drawings

CHROMOGENIC AND FLUOROGENIC SILANES AND USING THE SAME

CROSS REFERENCE TO RELATED APPLICATION

This is a continuation in part of copending Application Ser. No. 631,036, filed July 16, 1984, now abandoned.

FIELD OF THE INVENTION

The present invention is directed to chromogenic and fluorogenic silylation reagents for derivatization of protic materials. More particularly, the invention is directed to reactive silanes containing coumarin groups, as well as methods of making and using these silanes.

BACKGROUND OF THE INVENTION

Chromogens are materials which have the ability to impart a visualizable spectral characteristic to a compound, the absorption generally being in the near ultraviolet range. Fluorogens are a subclass of chromogenic materials which have the ability to impart a fluorescent or light-emitting spectral characteristic to a compound. In general, the fluorescence maxima is at a longer wavelength (less energetic) than the absorption. The ability to temporarily or permanently modify active hydrogen-containing materials (protic compounds) with a chromogenic or fluorogenic group has a multitude of applications.

For example, protic materials can be derivatized for recognition (visualization) by ultraviolet detectors in high pressure liquid chromatography, permanently bonded optical brightners for fabrics and plastics, and fluorometric biochemical assays, etc. Another conceivable application is to copolymerize these fluorescent silanes with other silanes to yield fluorescent silanes. Although monomeric silane materials theoretically represent a facile route for the derivatization of both molecular and macromolecular protic materials, such silanes with chromogenic or fluorogenic properties have generally not been available.

SUMMARY OF THE INVENTION

The chromogenic or fluorogenic silanes of the present invention comprise a reactive organosilane with an ether, urethane or urea linkage from one of the organo groups on the silane to a chromogenic or fluorogenic nucleus. Preferred silanes of the invention have a coumarin group nucleus and are represented by the following formula:

$$X_yR'_zSi(CH_2)_nL\text{-Cou}$$

wherein X is a displaceable or hydrolyzable group, such as halogen, lower (e.g. $C_1-C_6$) alkoxy, or dimethyamino group, which allows the silanes to derivatize protic materials; R' is an aliphatic or aromatic hydrocarbon group, preferably lower (e.g. $C_1-C_6$) alkyl or phenyl; L is an ether (O), urethane

(NCO)

or urea

(NCN)

linkage; Cou is a coumarin derivative; n=1 to 8; y=1 to 3 and z=0 to 2 such that y plus z equal 3.

Preferably, the coumarin derivative is a bicyclo coumarin nucleus which may be represented by the following formula:

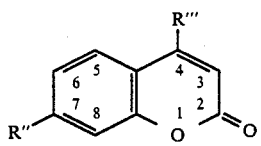

wherein R" and R''' may be, for example, hydrogen; hydroxyl; halogen; lower (e.g. $C_1-C_6$) alkyl; substituted lower alkyl, such as halogen-, hydroxyl- or amino-substituted lower alkyl; lower (e.g. $C_1-C_6$) alkoxy; amino or dimethylamino. One of R" or R''' must be or have a reactive group, such as a hydroxyl or amino group, to react with the reactive organosilane. For example, a preferred coumarin is methylumblliferone where R" is hydroxyl and R''' is methyl. Alternatively, the 4 position may be unsubstituted and the 5, 6, 7 or 8 position may be hydroxy substituted. Other positions may be substituted as well.

Silanes with an ether linkage to the coumarin may be produced by forming an alkenyl ether of coumarin followed by hydrosilylation, while the silanes having an urethane or urea linkage may be formed by reacting alkoxyfunctional silylisocyanates directly with a hydroxyl- or amino-substituted coumarin. The silanes of the invention may be used to derivatize protic materials such as fatty acids, amino acids and alcohols including hydroxy-containing steroids to give them chromogenic or fluorogenic properties.

DETAILED DESCRIPTION OF THE PREFERRED EMBODIMENTS

According to the invention the chromogenic or fluorogenic nucleus for the silanes is selected from the coumarin class of compounds, particularly hydroxy derivatives of the bicyclo coumarins. The preferred hydroxy derivative is methylumbelliferone, but examples of other such hydroxy derivatives include umbelliferone (7-hydroxycoumarin), 4-hydroxy-methylcoumarin, and the 5-, 6- or 8-hydroxycoumarins. Other coumarin derivatives useful in the present invention include those which can be synthesized by formation of an allyl ether followed by hydrosilylation (see K. Kaufman, *Journal of Organic Chemistry* 26: 117 (1961), and K. Kaufman et al, *Journal of Organic Chemistry*, 45: 738 (1980), or by reaction with an isocyanate functional silane such as hydroxymethyl or aminomethyl derivatives.

The coumarin class compound used as a nucleus is attached to a reactive organosilane by either an ether, urethane or urea linkage to form the chromogenic or fluorogenic silanes of the present invention. The reactive organosilanes which may be attached to the coumarin class nucleus include those which have at least one displaceable group which allows the compound to derivatize protic materials. Preferred organosilanes include the chlorosilanes and alkoxysilanes, but other reactive groups are possible such as bromosilanes. The remaining organo (R') groups on the reactive organosilanes may be aliphatic or aromatic hydrocarbons, preferably lower (e.g. $C_1$-$C_6$) alkyl or phenyl groups.

Two general methods may be used for synthesizing the chromogenic or fluorogenic silanes of the present invention, depending upon whether the linkage between the coumarin class nucleus and the reactive organosilane is an ether linkage or an urethane or urea linkage. Although other methods are possible, the most expedient method for forming silanes with an ether linkage to the coumarin compound involves the formation of an alkenyl ether of the coumarin compound followed by hydrosilylation. This method may be represented by the following equation in which an alkenyl ether is reacted with methylumbelliferone to form 7-[3(chlorodimethylsilyl)propoxy]methylcoumarin.

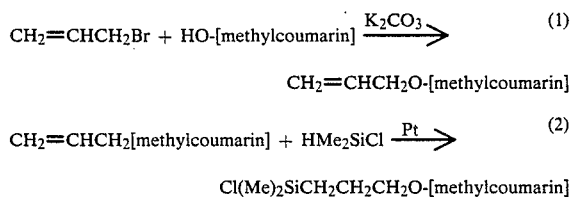

A bromosilane could also be used to react with a hydroxy coumarin by ether formation as by the following equation:

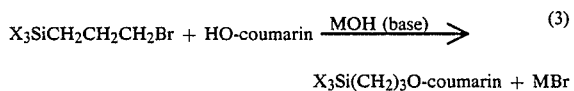

but this route is less desirable since in most instances a side reaction of the base with electronegative substituents on the silanes will occur.

Monofunctional chlorosilane materials of this type are useful, for example, for derivatization in high pressure liquid chromatography (HPLC) and in the formation of visualizable blocked intermediates useful in synthesis.

Chromogenic or fluorogenic silanes of the present invention having an urethane or urea linkage to the coumarin compound may be formed, for example, by reaction of reactive silylisocyanates, preferably an alkoxy functional silylisocyanate, directly with the coumarin compound. A reaction of this type may be represented by the following equation, in which triethoxysilylpropylurethane is reacted with methylumbelliferone with a tin catalyst to yield (N-triethoxysilylpropyl-)O-(4-methylumbelliferone)urethane.

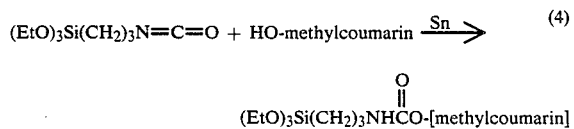

A parallel reaction in which the isocyanate reacts with an amino-substituted coumarin would proceed under the same conditions to yield an urea linked chromogenic silane.

Reaction of the coumarin compound with a chlorine functional silylisocyanate instead of an alkoxy functional silylisocyanate is not as satisfactory because of the low yield due to interaction of the chlorine with the hydroxyl group of the coumarin derivative. The silanes of the present invention having urethane linkages are generally better chromophores, but the protic nitrogen generally limits their utility to surface treatment applications, such as affinity chromatography.

The present invention will now be described in more detail with reference to the following specific, non-limiting examples:

EXAMPLE 1

7-[3(Chlorodimethylsilyl)Propoxy]4-Methylcoumarin

Step 1: Preparation of allyl ether of methylumbelliferone

A 1 liter 3 neck flask equipped with a mechanical stirrer, heating mantle and condensor is charged with 400 mls of acetone, 200 mls of tetrahydrofuran (THF), 83.1 g of 4-methylumbelliferone, 90 g of potassium carbonate and 60 mls of allyl bromide. The mixture was refluxed for 24 hours, filtered through glass wool, and concentrated until the pot temperature was 120 degrees C. The residue was dissolved in 200 mls of hot toluene, refiltered and poured into about 500 mls of hexane with rapid stirring. The isolated brownish-white product had a melting point of 87-90 degrees C. Structure was verified by NMR in $CDCl_3$ as the allyl ether of methylumbelliferone.

Step 2:

A glass pressure bottle was charged with 21.6 g of the allyl ether of 4-methylumbelliferone, 11 mls of dimethylmonochlorosilane, 25 mls of toluene and 0.1 cc of a 0.1M $H_2PtCl_6$ solution in tetrahydrofuran. The mixture was heated to 140 degrees C. at 40 psi for 15 hours. Toluene was removed by rotary evaporation. The title product was recovered in a yield of 27 g at greater than 70% purity as determined by proton NMR. A broad UV absorption spectrum was observed with maxima at 319.5, 281, 248 and 223 nanometers (nm). The extinction coefficient at 319.5 was greater than 20,000. Fluorescence spectra obtained after excitation at 384 nm gave maxima at 390 (v.s.), 421, 521, and 585 nm.

EXAMPLE 2

7-[3(Chlorodimethylsilyl)Propoxy]4-Methylcoumarin

Step 1: Preparation of allyl ether of methylumbelliferone.

A 3 L 3-necked flask fitted with overhead stirrer, thermometer, condenser and addition funnel was charged with 220 g (1.25 mol) of 7-hydroxy-4-methylcoumarin, 210 g (1.5 mol) $K_2CO_3$, 180 g (1.5 mol) allyl bromide and 600 ml DMSO. The contents were stirred, with a slight exotherm causing the pot temperature to rise to about 50 degrees C. After evolution of $CO_2$ started, the stirring continued for 6 hours. The reaction mixture was warmed to 50 degrees C. and stirring continued for an additional 4 hours until the evolution of $CO_2$ ceased. The contents were diluted with 800 ml ethyl acetate, transferred to a separatory funnel and washed twice with color water. The aqueous extract was extracted with ethyl acetate and combined with the main organic layer. The combined organic layer was washed with water, dried over sodium sulfate, concentrated to ⅓ of the volume and poured into a beaker. It deposited off-white flakes which were removed by filtration (130 g). The filtrate was diluted with an equal volume of hexane and allowed to stand. This yielded 110 g of the product, with a total yield of 240 g (89%).

Step 2:

A 1 L 3-necked flask fitted with condenser, thermometer and addition funnel was charged with 87 g (0.4 mol) of the allyl ether of methylumbelliferone formed by Step 1 and 200 ml toluene. While stirring the contents, 15 ml dimethylchlorosilane and 0.5 ml H$_2$PtCl$_6$ were added. With warming of the reaction mixture by an IR lamp, the reaction initiated at 70 degrees C. and quickly rose to 105 degrees C. with reflux. The addition of 40 additional grams of dimethylchlorosilane (0.5 mol total) was adjusted to produce gentle reflux (30 minutes), followed by stirring at 110 degrees C. for 1 hour. The reaction mixture was cooled to room temperature, and the toluene was removed under reduced pressure. The last traces of solvent were removed under high vacuum. The residue (120 g) was dissolved in 1200 ml of acetonitrile for storage and handling. The substitution of DMSO for THF as the solvent in Step 1 eliminated the need for pressure in Step 2 and made the second step generally run cleaner.

EXAMPLE 3

(N-Triethoxysilylpropyl)O-(4-Methylumbelliferone-)Urethane

Methylumbelliferone (88.1 g) and 600 mls of uninhibited tetrahydrofuran were charged in a 1 L single neck flask. The mixture was warmed until the methylumbelliferone dissolved. Isocyanatopropyltriethoxysilane (128.7 g) was charged and agitated, followed by the addition of 0.5 mls of dibutyltindilaurate. The mixture was refluxed for one week. Solvent was stripped by rotary evaporation. The white crystals were washed with two 500 ml portions of ether. Total yield of 180 g of the title compound (mp of 88-90 degrees C.). Characteristic urethane absorption was observed in the IR. A broad UV absorption spectrum was observed with maxima at 323.5, 281 and 223 nm. The extinction coefficient at 323.5 was greater than 20,000.

As an example of the use of the chromogenic silanes of the present invention, they may be used to derivatize amines or alcohols, such as by the following reaction:

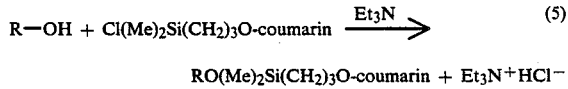

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

I claim:

1. A chromogenic or fluorogenic silane having the formula:

wherein X is a hydrolyzable group selected from the group consisting of halogen, C$_1$-C$_6$ alkoxy, and dimethylamino; R' is a C$_1$-C$_6$ alkyl or phenyl group; L is an ether (O), urethane

or urea

linkage; Cou is a bicyclo coumarin nucleus and L is linked to the coumarin nucleus at any unsubstituted position; n=1 to 8; y=1 to 3; and z=0 to 2, such that y plus z equals 3.

2. A silane according to claim 1 wherein the coumarin nucleus has the formula:

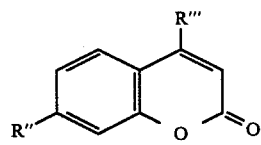

wherein one of R" and R''' is hydrogen, hydroxyl, halogen, C$_1$-C$_6$ alkyl, halogen-, hydroxyl- or amino-substituted C$_1$-C$_6$ alkyl, C$_1$-C$_6$ alkoxy, amino or dimethylamino, and L is linked to the coumarin nucleus at the other R" or R''' position.

3. A silane according to claim 1 wherein said coumarin nucleus is a methylumbelliferone nucleus.

4. A silane according to claim 1 wherein L is an ether linkage.

5. A silane according to claim 1 wherein L is an urethane or urea linkage.

6. 7-[3-(chlorodimethylsilyl)propoxy]methylcoumarin.

7. (N-triethoxysilylpropyl)O-(4-methylumbelliferone)urethane.

* * * * *

UNITED STATES PATENT AND TRADEMARK OFFICE
CERTIFICATE OF CORRECTION

PATENT NO. : 4,918,200
DATED : April 17, 1990
INVENTOR(S) : BARRY C. ARKLES

It is certified that error appears in the above-identified patent and that said Letters Patent is hereby corrected as shown below:

Col. 2, line 26, change "methylumblliferone" to -- methylumbelliferone -- .

Col. 4, line 60, change "color" to -- cold -- .

Signed and Sealed this

Second Day of April, 1991

*Attest:*

*Attesting Officer*

HARRY F. MANBECK, JR.

*Commissioner of Patents and Trademarks*